United States Patent [19]
Falkenburg

[11] 3,996,339
[45] Dec. 7, 1976

[54] METHOD FOR THE CHEMICAL CONVERSION IN GAS MIXTURES

[75] Inventor: Rudy André Falkenburg, Eindhoven, Netherlands

[73] Assignee: U.S. Philips Corporation, New York, N.Y.

[22] Filed: Dec. 3, 1974

[21] Appl. No.: 529,124

[30] Foreign Application Priority Data
Dec. 4, 1973  Netherlands ............... 7316555

[52] U.S. Cl. .............. 423/405; 23/232 E; 23/254 E; 23/281; 252/188
[51] Int. Cl.² ............ C01B 21/24; C09K 3/00; G01N 31/00
[58] Field of Search ......... 252/188, 397; 23/254 E, 23/232 E, 281; 423/405; 260/689; 206/84

[56] References Cited
UNITED STATES PATENTS

| | | | |
|---|---|---|---|
| 1,356,029 | 10/1920 | Wesson | 252/188 |
| 3,361,661 | 1/1968 | Schulze | 204/195 T |
| 3,382,033 | 5/1968 | Kitagawa | 423/239 |
| 3,659,100 | 4/1972 | Anderson et al. | 23/252 R |

OTHER PUBLICATIONS

"Quantitative Measurement of Nitrogen Dioxide in Gaseous Mixtures," Anal. Abst. No. 1070, vol. 27 (Aug. 1974).
"Quantitative Measurement of Ammonia in Gaseous Mixtures," Anal. Abst. No. 1071, vol. 27 (Aug. 1974).

Primary Examiner—Norman Yudkoff
Assistant Examiner—Barry I. Hollander
Attorney, Agent, or Firm—Frank R. Trifari; Norman N. Spain

[57] ABSTRACT

Method of reducing $NO_2$ to $NO$ with a granular mixture of ferrous sulfate and an alkaline hydrogen sulfate in a molar ratio of 3:1 to 1:1.

2 Claims, 4 Drawing Figures

METHOD FOR THE CHEMICAL CONVERSION IN GAS MIXTURES

The invention relates to an apparatus for chemical conversion of gas mixtures.

Such an apparatus comprisng a container which has a gas inlet and a gas outlet and is filled with a granular reagent for maximum reaction surface area is described inter alia in U.S. Pat. No. 3,361,661.

In apparatus of this type a given constituent of a gas mixture is to be removed or to be converted, for example by reduction or oxidation. In the aforementioned patent specification the concentrations of ozone and of sulphur dioxide in a gas mixture are to be determined. Since in this determination the said constituents interfere with one another, in one analysis the ozone and in the other analysis the sulphur dioxide is removed. Ozone is removed in a container filled with granular ferrous sulphate heptahydrate ($FeSo_4.7H_2O$).

Such an apparatus filled with ferrous sulphate may also be used for converting $NO_2$ into NO.

It was found in practice that the said apparatus has disadvantages, for the conversion of $NO_2$ into NO is not quantitative. In addition, the properties of the ferrous sulphate deteriorate at a comparatively rapid rate, because the ferrous sulphate is hydrolysed and because the $NO_2$ is absorbed at the granular material.

It is an object of the present invention to provide a reagent for use in such an apparatus which has a long useful life and ensures complete conversion.

According to the invention an apparatus for the chemical conversion of gas mixtures which comprises a container having an inlet and an outlet and filled with a granular ferrous sulphate composition is characterized in that the composition is a mixture of ferrous sulphate and an alkali metal acid sulphate in a molar ratio from 3:1 to 1:1. These limits of the mixing ratio are critical; below 1:1 the reduction rapidly falls with increasing proportions of alkali metal acid sulphate. The upper limit of 3:1 is the limit of stability; at higher values hydrolysis occurs.

The said granular composition may be used as such, however, preferably a granular inert carrier material is used on the surface of which the mixture of ferrous sulphate and alkali metal acid sulphate is disposed.

The inert carrier material may be pumice, silica, quartz or polytetrafluoroethylene, preferably in a large-surface-area configuration.

The advantage of the apparatus according to the invention is that the desired conversions take place quantitatively while in addition the useful life is very long. The apparatus has a satisfactory mechanical strength, when the active material is disposed on an inert carrier its adherence is satisfactory, and the apparatus is capable of withstanding extreme conditions, such as large humidity and desiccation. It is effective even at room temperature and up to about 50° C.

It is permeable to $SO_2$, NO, $H_2S$ and mercaptanes, and it is not poisoned by sulphur compounds.

In a practical embodiment an apparatus according to the invention is filled with pumice having a grain size of 6 to 7 mesh (1 to 2 mm) and a specific surface area of from 100 to 200 m²/g which is impregnated with a mixture of $FeSO_4.7H_2O$ and $KHSO_4$ in a molar ratio of 1:1.

Impregnation is effected by wetting the grains in vacuo with a solution of the said salts and subsequent drying by evaporation.

At a temperature between 20° and 45° C the following reactions take place:

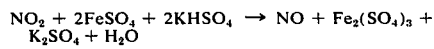

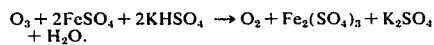

An embodiment of the invention will now be described, by way of example, with reference to the accompanying diagrammatic drawings.

IN THE DRAWINGS

Figure 1:
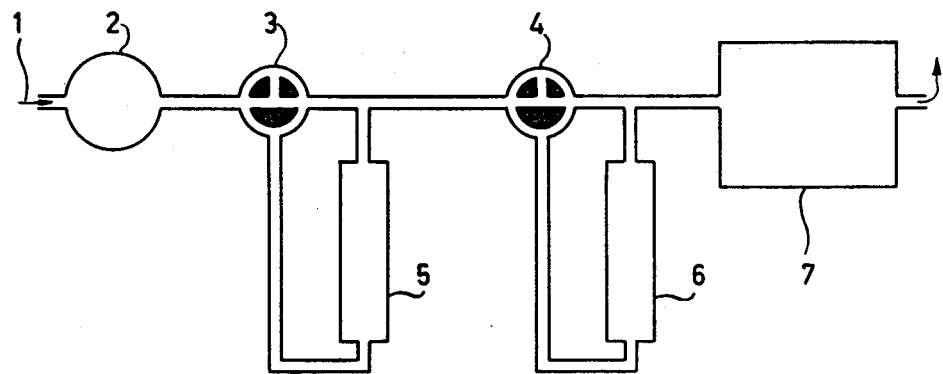
FIG. 1 is a diagrammatic view of an apparatus according to the invention showing the reductor and oxidator in series with the source of $NO_2$.

Referring now to FIG. 1, a gas stream 1 comprises pure air which is supplied at a rate of 150 cm³/minute. A supply source which delivers gaseous $NO_2$ at a rate of 0.065/μg/minute is indicated by 2. As a result, the gas stream contains 0.23 part of $NO_2$ per million parts of air. A reductor 5 according to the invention and an oxidator 6 having a 100% oxidation efficiency can be arranged in series with the source of $NO_2$ by three-way valves 3 and 4. The $NO_2$ content in the emerging gas stream is determined by means of a coulometer 7. This coulometer does not determine the content of NO.

Figure 4:
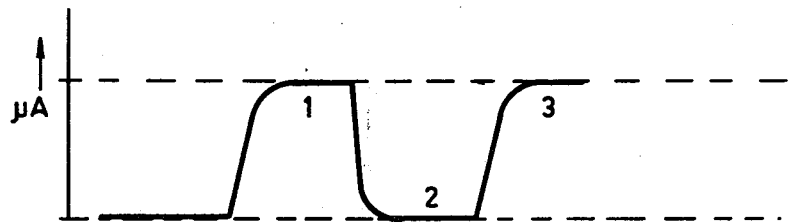
FIG. 4 is a curve showing $NO_2$ content in the emerging gas stream for each of the three reductor-oxidizer combinations of the apparatus of the invention.

In the positions of the valves shown in FIG. 1 the air which issues from 2 and contains a metered amount of $NO_2$ is measured. In the practical embodiment used a signal of 1.98 /μA was produced. FIG. 4 shows the output signal from the coulometer 7.

Figures 2, 3:
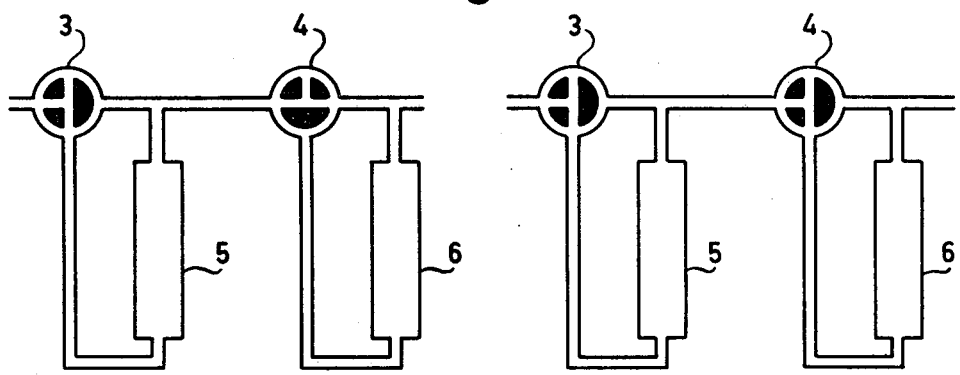
FIG. 2 is a diagrammatic view of a portion of the apparatus of the invention in which the reductor is in circuit with the source of $NO_2$.
FIG. 3 is a diagrammatic view of a portion of the apparatus of the invention in which the reductor is in circuit with the source of $NO_2$ and the oxidizes is in circuit with the reduced gas.

In the positions of the three-way valves shown in FIG. 2 the reductor 5 is in circuit. The $NO_2$ is completely reduced to NO. The signal now becomes zero. Then the valves are set to the positions shown in FIG. 3. The reduced gas then is oxidised to become $NO_2$ again. The signal 1.98/μA is again fully obtained, which proves that no absorption or other losses or the nitrogen oxide occur in the apparatus.

The reductor according to the invention was a tube of length 10 cm and diameter 13 mm. It contains 6 g of reducing agent, i.e. pumice grains of grain size from 1 to 2 mm to which 1 g of ferrous sulphate and 0.3 g of potassium hydrosulphate $KHSO_4$ had been applied.

In the apparatus described the said reductor gave a yield of more than 99% for more than 1,000 hours.

What is claimed is:

1. In a method for the chemical conversion of $NO_2$ in a gas mixture to NO by reduction by passing the gas mixture through a container filled with an inorganic reducing composition, the improvement wherein said inorganic reducing composition is a mixture of ferrous sulfate and an alkali metal acid sulfate in a molar ratio of between 3:1 and 1:1.

2. The method of claim 1 wherein the inorganic reducing composition is applied to the surface of an inert carrier material.

* * * * *